(12) United States Patent
Cempini et al.

(10) Patent No.: US 9,730,825 B2
(45) Date of Patent: Aug. 15, 2017

(54) WEARABLE EXOSKELETON DEVICE FOR HAND REHABILITATION

(71) Applicant: SCUOLA SUPERIORE S.ANNA, Pisa (IT)

(72) Inventors: Marco Cempini, Terricciola (IT); Nicola Vitiello, Pontedera (IT); Francesco Giovacchini, Pisa (IT); Stefano Marco Maria De Rossi, Mirano (IT); Tommaso Lenzi, Chicago, IL (US); Azzurra Chiri, Pontedera (IT); Maria Chiara Carrozza, Pisa (IT)

(73) Assignee: SCUOLA SUPERIORE S. ANNA, Pisa (IT)

( * ) Notice: Subject to any disclaimer, the term of this patent is extended or adjusted under 35 U.S.C. 154(b) by 242 days.

(21) Appl. No.: 14/422,488

(22) PCT Filed: Aug. 26, 2013

(86) PCT No.: PCT/IB2013/056894
§ 371 (c)(1),
(2) Date: Feb. 19, 2015

(87) PCT Pub. No.: WO2014/033613
PCT Pub. Date: Mar. 6, 2014

(65) Prior Publication Data
US 2015/0223959 A1      Aug. 13, 2015

(30) Foreign Application Priority Data

Aug. 28, 2012   (IT) .................... PI2012A0094

(51) Int. Cl.
*A61F 5/01*      (2006.01)
*A61H 1/02*     (2006.01)

(52) U.S. Cl.
CPC .......... *A61F 5/013* (2013.01); *A61H 1/0285* (2013.01); *A61H 1/0288* (2013.01);
(Continued)

(58) Field of Classification Search
CPC .. A61F 5/05875; A61F 5/0118; A61F 13/105; A61F 5/10; A61F 5/05866; A61F 5/50; A61F 5/013; A61F 2005/0155; A41D 19/01588; A41D 13/087; A61H 1/0285; A61H 1/0288; A61H 2201/1215; A61H 2201/1638; A61H 2201/165; A61H 2201/1664; A61H 2201/1673
See application file for complete search history.

(56) References Cited

FOREIGN PATENT DOCUMENTS

EP           2436358 A1      4/2012

OTHER PUBLICATIONS

International Search Report mailed Jun. 10, 2014, corresponding to International Patent Application PCT/IB2013/056894.

*Primary Examiner* — Ophelia A Hawthorne
(74) *Attorney, Agent, or Firm* — Ladas & Parry LLP

(57) ABSTRACT

An exoskeleton device for assisting the movement of a metacarpal-phalangeal joint of a hand in a flexion/extension plane Γ of the joint, including a metacarpal support arranged integrally with a metacarpal portion of the hand, a phalangeal support having a fastening link for fastening to a proximal phalanx, a kinematical chain between the metacarpal support and the phalangeal support arranged to provide and carry out a rotation of the phalangeal support with respect to the metacarpal support.

9 Claims, 13 Drawing Sheets

(52) U.S. Cl.
CPC ............... *A61H 2201/1215* (2013.01); *A61H 2201/165* (2013.01); *A61H 2201/1638* (2013.01); *A61H 2201/1664* (2013.01); *A61H 2201/1673* (2013.01)

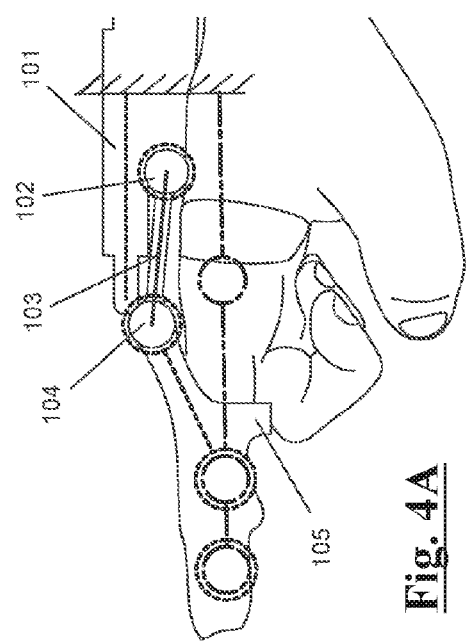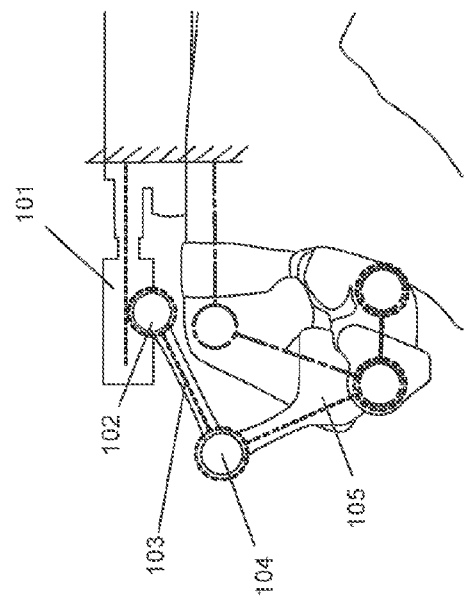

WEARABLE EXOSKELETON DEVICE FOR HAND REHABILITATION

This application is a 371 of PCT/IB2013/056894, filed on Aug. 26, 2013, which claims priority to Italian Application No. PI2012A000094 filed Aug. 28, 2012.

FIELD OF THE INVENTION

The present invention relates to a wearable mechatronic exoskeleton for neuro-rehabilitation of the limb of a patient, in particular for orthopedic and neurological rehabilitation of the hand. Further applications relate to the use of the exoskeleton for controlling and operating a remote device (teleoperation) and for studying the biomechanics of the hand.

A particular aspect of the invention relates to an exoskeleton for the region of the metacarpal-phalangeal joint of the hand, in particular of the thumb and of the index finger.

Another particular aspect of the invention relates to an exoskeleton for the region of the wrist of the hand.

DESCRIPTION OF THE PRIOR ART

As well known, a problem faced by many mechanical wearable devices (haptic or exoskeleton devices) is to provide a outer kinematic matching of the device with the anthropometry of the human hand and at the same time to allow an exchange of physical interactions (forces/couples) without jeopardizing maximum safety for the human user.

In case of assistance and rehabilitation, the need is felt of a structure capable of bearing and detecting external loads and transmitting them in a comfortable and safe way to the human joints. One of the risks is a to introduce too many constraints to the mechanical structure of the device.

In fact, an exoskeleton structure that is strong enough is also very stiff when coupled with the human kinematic structure, and then cannot operate with efficiency, owing to many effects, such as the misalignment of the axes of the robotic joints with the human joints and the variability of the conformation external of the human body, jeopardizing the operation of the device.

The particular case of the hand has such problems in a very extended way, owing to its wide mobility and the small size of its segments. For this reason, the research for solutions to this problem is very desirable in rehabilitation, where therapies mediated by robotic apparatus are the most used for their large potentiality; in particular, mechanical wearable devices are desirable that allow the assistance to the only anatomical joints of the fingers of the patient, without impeding natural movements and without causing excessive discomfort.

A very high interest is concentrated on the functional rehabilitation of the grip of the hand, such as a cylindrical grip and precision grip. For this reason it is necessary that the exoskeleton device does not impede the palm of the hand and bending the wrist of the patient for keeping the position of the hand with respect to arm during the grip anatomically correct.

An exoskeleton device for the arm that comprises an exoskeleton for the hand is described in WO2009016478A2, which allows assisting the movement of the metacarpal-phalangeal joint and of the interphalangeal joints of the hand.

Such reference provides the alignment of the axes of the phalanxes of the exoskeleton joints with the axes of the interphalangeal joints, in order to reduce constraint forces on the joints and to improve kinematic compatibility between the movement of the fingers and those of the exoskeleton.

Concerning the metacarpal-phalangeal joint, a backing member which can be fixed out of the metacarpus and a shell element which can be fixed to the proximal phalanx are provided, pivotally connected to each other by a metacarpal-phalangeal exoskeleton joint. Such solution, however, does not allow to this exoskeleton joint the alignment with the metacarpal-phalangeal joint, and therefore, for this joint, there is not the same kinematic compatibility that there is for the interphalangeal joints, causing the presence of constraint forces that reduce remarkably the comfort of use.

Furthermore, the exoskeleton cited is not completely implemented in case of different anthropometric hand sizes, causing a possible increase of the constraint forces on the metacarpal-phalangeal joints.

Another drawback high of the device above cited, relates to a low adaptation of the exoskeleton joint to the actual flexion/extension rotation axis of the metacarpal-phalangeal joint, that, as well known, is unsteady during this rotation movement.

Another exoskeleton for the hand of known type is disclosed in EP2436358. In this case a support for fastening the exoskeleton to the back of the hand of the user and five mechanical fingers connected to the support are provided. Each mechanical finger comprises a stiff proximal element integral to the support and an intermediate stiff element mechanically connected to the stiff proximal element. More in detail, the intermediate stiff element can rotate in a forced way with respect to the stiff proximal element. In fact the intermediate stiff element comprises an arm having an end forced to move in an arc-shaped rail guide made in the stiff proximal element. An adjustable connection is also provided whose length varies responsive to the movement of the intermediate stiff element with respect to the stiff proximal element.

Since the centre of rotation the arc-shaped rail guide is located approximately at the centre of rotation of the anatomical metacarpal-phalangeal joint, said exoskeleton causes a lower presence of constraint forces on the anatomical joint than the WO2009016478A2 exoskeleton.

However, also in this case an actual elimination of the constraint forces on the metacarpal joint is substantially impossible. This is due both to the fact that the stiff proximal element is integral to the fastening support to the back of the hand and to the fact that the radius of the arc-shaped rail guide cannot be altered. Therefore, the exoskeleton described in EP2436358 does not allow adaptation to the structure to various anthropometric hand sizes, nor it can follow the centre of rotation of the metacarpal-phalangeal joint that, as said, changes position during the use.

Therefore also the exoskeleton described in EP2436358 is not very comfortable for a user and it can be also detrimental for the joints of the fingers of the hand, owing to the generation of the above described constraint forces.

SUMMARY OF THE INVENTION

It is therefore a feature of the present invention to provide a device for overcoming the above described drawbacks of the exoskeleton devices of the prior art, and, in particular for assisting the flexion/extension of the joints of a hand by means of a pure torque that does not generate constraint forces on the metacarpal-phalangeal and interphalangeal joints, moving them for their whole natural workspace.

It is also a feature of the present invention to provide such a device that can be adapted to different anthropometric hand sizes.

It is a further feature of the present invention to provide such a device that is compatible with the three-dimensional configuration of the carpal-metacarpal joint of the thumb finger of the hand, i.e. that allows the free movement of opposition and of ab/adduction of the thumb.

It is another feature of the present invention to provide such a device that allows the free movements of flexion/extension and of ab/adduction to the metacarpal-phalangeal joints of the fingers of the hand.

It is also a feature of the present invention to provide such a device that is adaptable to an unsteady anatomical axis during the flexion/extension movement of the metacarpal-phalangeal joint.

It is also a feature of the present invention to provide such a device that presents a minimum encumbrance and a weight less than the prior art.

It is still a feature of the present invention to provide such a device that provides assistance to the flexion/extension of the anatomical joint of the wrist and that ensures also free ab/adduction movements.

These and other objects are achieved by an exoskeleton device for assisting the movement of a metacarpal-phalangeal joint of a hand in a flexion/extension plane Γ of the joint, the metacarpal-phalangeal joint arranged for carrying out a rotation θ about an axis z substantially orthogonal to the flexion/extension plane;
comprising:
   a metacarpal support arranged to be kept integral to a metacarpal portion of the hand;
   a phalangeal support having means for fastening to a proximal phalanx;
   a kinematical chain between the metacarpal support and the phalangeal support to provide and carrying out a rotation of the phalangeal support with respect to the metacarpal support;
said kinematical chain between the metacarpal support and the phalangeal support comprising:
   a metacarpal slide arranged to translate with respect to the metacarpal support along a predetermined line γ arranged in the flexion/extension plane Γ;
   a stiff link pivotally connected to the metacarpal slide by a first pivotal constraint;
   a second pivotal constraint arranged to connect pivotally the stiff link to the phalangeal support;
   an actuating means for causing a first rotation to the stiff link at the first pivotal constraint and a second rotation to the phalangeal support at the second pivotal constraint.

In particular, the actuating means is configured for zeroing the constraint forces of the exoskeleton device on the metacarpal-phalangeal joint versus the rotation θ, for any position of the metacarpal-phalangeal joint with respect to the exoskeleton device within a predetermined range.

This way, instead of seeking a coincidence between the metacarpal-phalangeal joint axis and the axis of the exoskeleton, according to the invention, a kinematical chain between the metacarpal support and the phalangeal support is made in such a way that at the relative position between the metacarpal-phalangeal joint and the exoskeleton device, within a predetermined range, the constraint forces of the exoskeleton device on the metacarpal-phalangeal joint are zero versus the rotation θ of the anatomic metacarpal-phalangeal joint.

In particular, the exoskeleton device, according to the invention, allows that two stiff links are actuated without generating constraint forces on the metacarpal-phalangeal joint, whichever is the instant position of the axis z about which the metacarpal-phalangeal joint rotates. Such aspect is particularly advantageous with respect to the exoskeletons of the prior art, since it allows the exoskeleton of the present invention to adapt to the different positions that the rotation axis z assumes during the rotation of the metacarpal-phalangeal joint. Furthermore, the exoskeleton, according to the present invention, can adapt automatically to different anthropometric sizes, ensuring that the metacarpal-phalangeal joint is not subject to undetermined constraint forces.

Preferably, the second pivotal constraint is the only element provided between the stiff link and the phalangeal support.

Advantageously, the first rotation and the second rotation of the first and the second pivotal constraints are made by means of respective pulleys arranged at the first and the second pivotal constraints and by at least one cable that causes the pulleys to rotate. This way, the rotation of the phalangeal support can be remotely actuated, for example by means of Bowden cables.

In particular, the actuating means remotely comprises a rotor arranged to cause the first rotation to the first pivotal constraint and at least one cable arranged to connect the first and the second pivotal constraints, such that the first and the second rotation are synchronous to each other. In this case, the first pivotal constraint, in particular the first pulley, is idle and the second pivotal constraint is integral to the phalangeal support, in order to transmit the rotation of the phalangeal support about the second pivotal constraint.

In particular, the pulleys have a same radius, in such a way that not only the constraint forces caused by the operation of the rotation of the phalangeal support are zeroed, but also possible constraint forces caused by the beats of the Bowden cable, in particular constraint moments at the pulleys, are not generated.

In a possible embodiment the device is configured for assisting the metacarpal-phalangeal joint of the index finger of the hand, and comprises a kinematical ab/adduction chain of the index finger located between the metacarpal support and the slide, the kinematical ab/adduction chain of the index finger being configured for assisting the movement of the metacarpal-phalangeal joint in an ab/adduction plane of the metacarpal-phalangeal joint substantially orthogonal to the flexion/extension plane Γ, in such a way that the exoskeleton device can always lay in the flexion/extension plane Γ.

In particular, the kinematical ab/adduction chain of the index finger comprises:
   an ab/adduction slide arranged to translate with respect to the metacarpal support along a predetermined line ϵ arranged in the ab/adduction plane;
   an ab/adduction pivotal constraint by which the metacarpal slide of the exoskeleton device is pivotally connected to the slide of the kinematical chain.

This way, owing to the co-presence of the slide more complete movements of ab/adduction can be carried out, i.e. similar to the real ones, such as the conical rotation of the index finger obtained by a combination of the flexion/extension and of the ab/adduction of the index finger same.

In another possible embodiment the device is configured for assisting the metacarpal-phalangeal joint of the thumb finger of the hand, comprising a kinematical chain of the thumb located between the metacarpal support and the stiff link. In particular, the kinematical chain of the thumb is configured for assisting the flexion/extension and ab/adduction movements of a carpal-metacarpal joint of the thumb. Such kinematical chain of the thumb comprises:
- a first shaft arranged to rotate about its own axis with respect to the metacarpal support, by a pivotal connection;
- a first segment pivotally connected to the shaft by a first pivotal constraint;
- a second segment pivotally connected to the first segment by a second pivotal constraint;
- a second shaft arranged to rotate about its own axis with respect to the second segment, by a pivotal connection;
- a slide pivotally connected to the second shaft by a pivotal constraint, the slide arranged to translate with respect to the pivotal constraint along a predetermined line λ and being also connected to the stiff link.

This way, the exoskeleton is compatible with the three-dimensional configuration of the carpal-metacarpal joint of the thumb finger of the hand, allowing the free movement of opposition and of ab/adduction of the thumb.

In a possible embodiment a serial mechanism for the wrist is further provided, operatively connected to the metacarpal support, arranged to assist the flexion/extension of the anatomical joint of the wrist, ensuring also free ab/adduction movements.

Such serial mechanism for the wrist may comprise:
- an ulnar support arranged to be kept integral to a distal portion of the forearm;
- an ulnar slide adapted to translate with respect to said ulnar support along a predetermined line δ substantially parallel to the longitudinal direction of the forearm;
- an articulated quadrilateral comprising:
  - a first connecting rod and a second connecting rod, parallel to each other and arranged in a direction substantially parallel to the line δ;
  - a first segment pivotally connected to the slide by a pivotal constraint;
  - a second segment rigidly connected to the metacarpal support.

In particular, the first and second segments can be arranged to connect between them the ends of the connecting rods by means of four passive spherical joints, in such a way that the metacarpal support can rotate with respect to the ulnar support about an axis whose position is not determined, adapting passively to the rotation of the anatomical joint of the wrist, according to the two axes that are perpendicular to the longitudinal direction of the forearm, without causing residual constraint forces.

Advantageously, a second serial mechanism is provided that is operatively connected to the metacarpal support and is arranged to reinforce the coupling between the ulnar support and the metacarpal support.

Such second serial mechanism may comprise:
- a rotatable slide arranged to translate with respect to the ulnar support along a predetermined line σ and to rotate about the line σ with respect to the ulnar support, said line σ being substantially perpendicular to the line δ;
- a further slide arranged to translate with respect to the rotatable slide along a predetermined line ρ substantially perpendicular to the line σ, said slide being connected to the metacarpal support by a ball joint.

Preferably, the exoskeleton device is configured for assisting the movement of a metacarpal-phalangeal joint of the index finger and of the thumb, as well as of the wrist of a hand as above defined.

According to another aspect of the invention, an exoskeleton device for assisting the movement of a metacarpal-phalangeal joint and of the wrist of a hand, said metacarpal-phalangeal joint arranged for carrying out a rotation θ about an axis z substantially orthogonal to a flexion/extension plane Γ of the joint, comprises:
- a metacarpal support arranged to be kept integral to a metacarpal portion of the hand;
- a phalangeal support having means for fastening to a proximal phalanx;
- a kinematical chain between the metacarpal support and the phalangeal support to provide and carrying out a rotation of the phalangeal support with respect to the metacarpal support;
- a serial mechanism for the wrist operatively connected to the metacarpal support and arranged to assist the flexion/extension of the anatomical joint of the wrist, ensuring also free ab/adduction movements, said serial mechanism for the wrist comprising an ulnar support arranged to be kept integral to a distal portion of the forearm;

In particular, the serial mechanism for the wrist comprises furthermore:
- an ulnar slide adapted to translate with respect to the ulnar support along a predetermined line δ substantially parallel to the longitudinal direction of the forearm;
- an articulated quadrilateral comprising:
  - a first connecting rod and a second connecting rod, parallel to each other and arranged in a direction substantially parallel to the line δ;
  - a first segment pivotally connected to the slide by a pivotal constraint;
  - a second segment rigidly connected to the metacarpal support;
- said first and the second segment arranged to connect between them the ends of the connecting rods by means of four passive spherical joints;
- in such a way that the metacarpal support can rotate with respect to the ulnar support about an axis whose position is not determined, the articulated quadrilateral being adaptable passively to the rotation of the anatomical joint of the wrist, according to both the axes that are perpendicular to the longitudinal direction of the forearm, without causing residual constraint forces.

In this case, a second serial mechanism can be also provided that is operatively connected to the metacarpal support and is arranged to reinforce the coupling between the ulnar support and the metacarpal support, the second serial mechanism comprising:
- a rotatable slide arranged to translate with respect to the ulnar support along a predetermined line σ and to rotate with respect to the ulnar support about the line σ, said line σ being substantially perpendicular to the line δ;
- a slide arranged to translate with respect to the rotatable slide along a predetermined line ρ substantially perpendicular to the line σ, said slide being connected to the metacarpal support by a ball joint.

BRIEF DESCRIPTION OF THE DRAWINGS

Further characteristic and/or advantages of the wearable exoskeleton device for rehabilitation of the hand, according to the present invention will be made clearer with the following description of an exemplary embodiment thereof, exemplifying but not limitative, with reference to the attached drawings in which:

FIGS. 4A and 4B show the exoskeleton device, mounted to the index finger of a hand, respectively in its extended and flexed configurations;

DESCRIPTION OF A PREFERRED EXEMPLARY EMBODIMENT

Figure 1A:
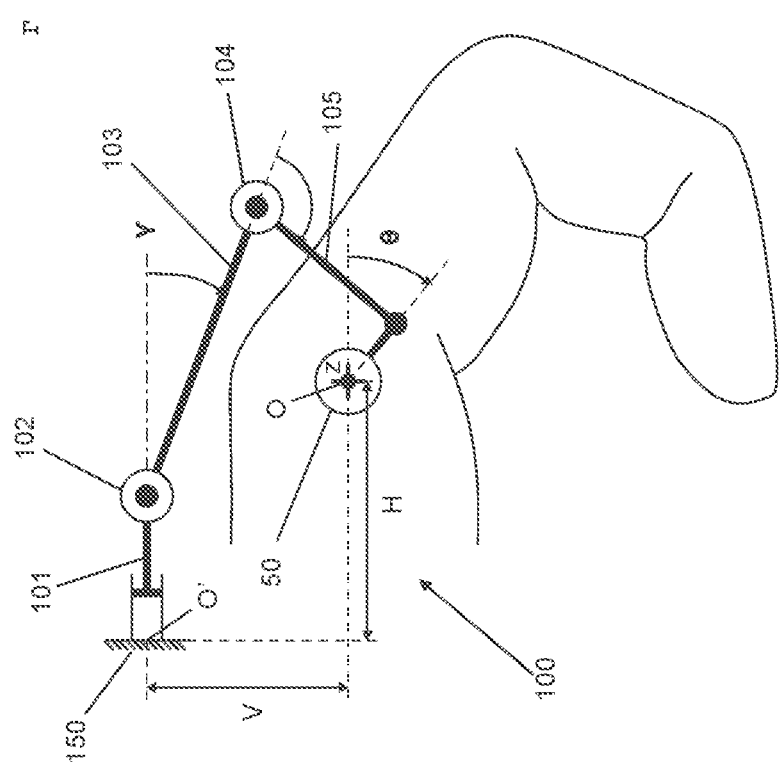
FIG. 1 shows a diagrammatical view of the exoskeleton device, according to the invention, for assisting the movement of a metacarpal-phalangeal joint of a hand in a flexion/extension plane of the joint same.

In FIG. 1A a diagrammatical view is shown of an exoskeleton device 100, according to the invention, for assisting the movement of a metacarpal-phalangeal joint 50, i.e. between the metacarpal bone and proximal phalanx of the finger of a hand in a flexion/extension plane of the joint same. The exoskeleton device 100 comprises:
- a metacarpal support 150 arranged to be kept integral to a metacarpal portion of the hand;
- a slide 101 arranged to provide an axial sliding movement along a predetermined line $\gamma$ with respect to the metacarpal support 150;
- a stiff link 103 pivotally connected to the slide 101 by a first pivotal constraint 102;
- a phalangeal support 105 pivotally connected to the stiff link 103 by a second pivotal constraint 104;
- an actuating means for causing a first rotation to the stiff link 103 and a second rotation to the phalangeal support 105 respectively at the first 102 and second 104 pivotal constraint.

The presence of the slide 101 provides a sufficient lability to the system, and the two rotational couplings 102 and 104, even if none of them is coincident with the anatomical axis of the metacarpal-phalangeal joint, determine a minimum and in particular zero, constraint forces that are transmitted to the joint.

Indicating as $\Gamma$ the plane of flexion/extension containing the sliding axial, the flexion/extension movement that the metacarpal-phalangeal joint 50 can carry out consists of a rotation $\theta$ about an axis z that is substantially orthogonal to the flexion/extension plane $\Gamma$.

Defining then a point O as the intersection between the rotation axis z of the joint 50 and plane $\Gamma$, and a point O' as the origin of the axial sliding movement of the slide, the relative coordinates between O and O' are H and V, respectively in a direction parallel and in a direction which is orthogonal to the line $\gamma$.

Figure 1B:
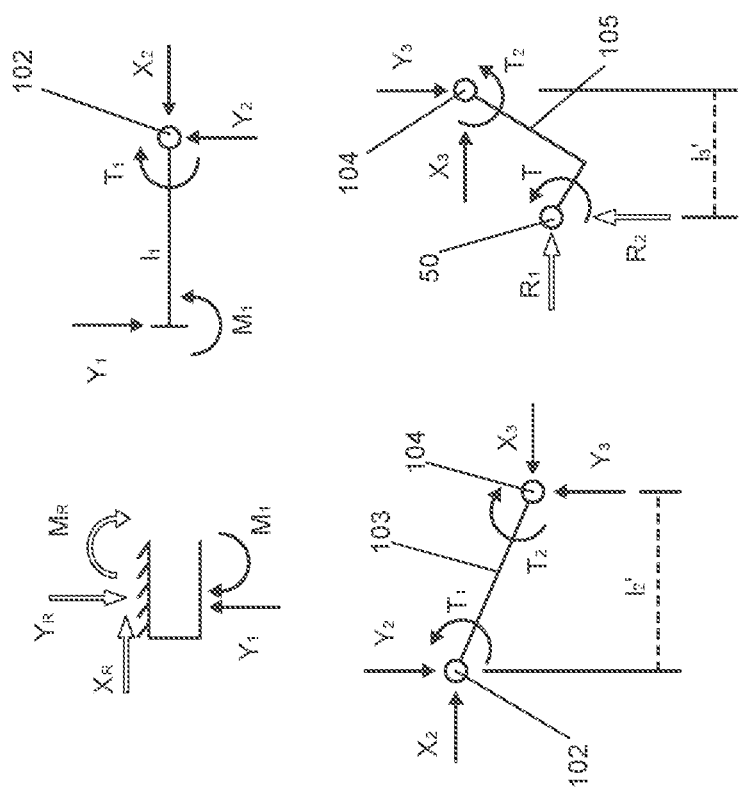

A diagrammatical view of the forces in play is shown in FIG. 1B. From the figure the following relations can be determined:

$$\begin{cases} Y_R = Y_1 \\ X_R = X_1 = 0 \\ M_R = M_1 \end{cases}$$

$$\begin{cases} Y_2 = Y_1 \\ X_2 = 0 \\ M_1 + Y_1 l_1 = T_1 \end{cases}$$

$$\begin{cases} Y_3 = Y_2 \\ X_3 = X_2 = 0 \\ T_1 + Y_2 l'_2 = T_2 \end{cases}$$

$$\begin{cases} R_2 = Y_3 \\ R_1 = -X_3 = 0 \\ T + T_2 = R_2 l'_2 \end{cases}$$

Starting from the previous equations, the torques $T_1$ and $T_2$ caused by the actuating means to the first pivotal constraint 102 and to the second pivotal constraint 104 are equal, then the constraint forces present on the constraint anatomical 50 are zero, versus the rotation $\theta$, within a predetermined range of H and V.

Figure 2:
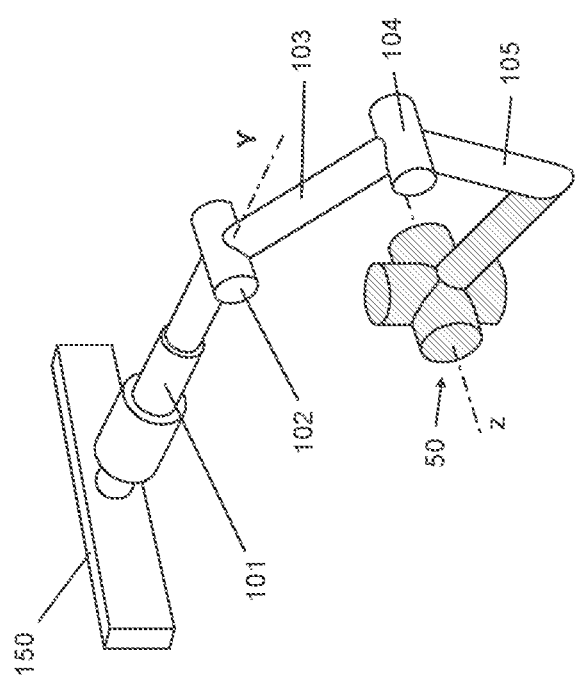
FIG. 2 shows a diagram of an exoskeleton device, according to the invention, mounted to the index finger of a hand.

In FIG. 2 the conceptual pattern is shown of an exoskeleton device 100, according to the invention, mounted to the index finger of a hand. For the sake of clarity, the anatomical parts have been hatched.

Figure 3:
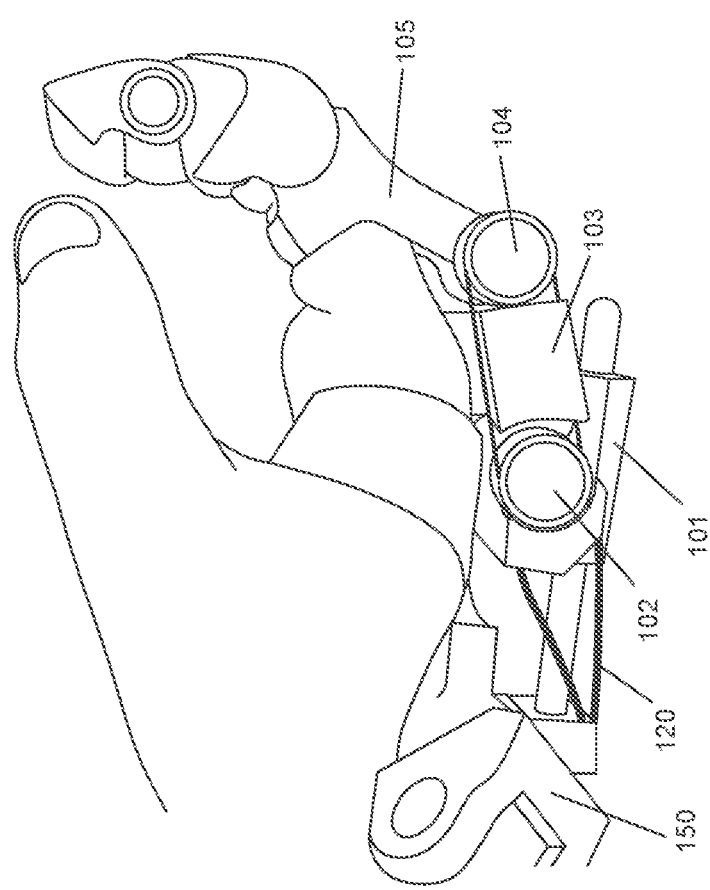
FIG. 3 shows a possible exemplary embodiment of the exoskeleton device of FIG. 2 applied to the index finger of the hand.

In FIG. 3 a possible exemplary embodiment is shown of the exoskeleton device 100 applied to the index finger of the hand. In this exemplary embodiment, the rotational constraints 102 and 104 are made by means of idle pulleys and the actuating means consists of Bowden cables 120 whose inner wires are wound about such pulleys 102 and 104.

In the FIGS. 4A and 4B the exoskeleton device 100 is shown, mounted to the index finger of a hand, respectively in its extended and flexed configurations. With the dashed line the chain of the exoskeleton joints is indicated, whereas with the dash-dot line the chain of the anatomic joints is indicated.

Figure 5:
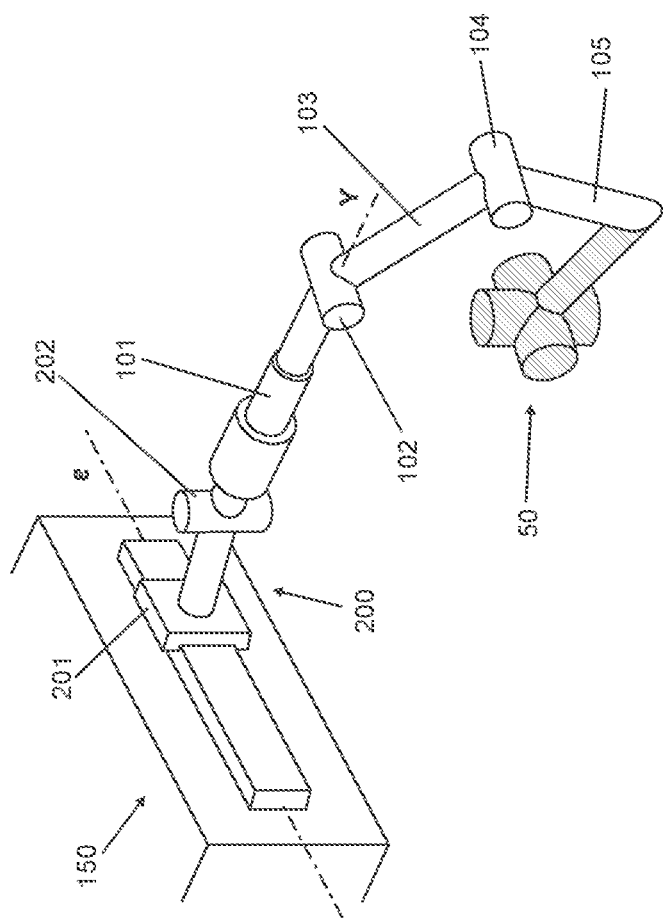
FIG. 5 shows a possible exemplary embodiment of the exoskeleton device of FIG. 2.

In FIG. 5 a possible exemplary embodiment is shown of the exoskeleton device 100 shown in FIG. 2, in which between the metacarpal support 150 and the slide 101 a kinematical chain 200 is located for the exoskeleton device 100 to follow passively the movement of ab/adduction of the metacarpal-phalangeal joint 50. Such kinematical chain 200 comprises:
- a slide 201 arranged to provide an axial sliding movement with respect to the metacarpal support 150 along a predetermined line $\epsilon$ arranged in the ab/adduction plane of the metacarpal-phalangeal joint;
- a pivotal constraint 202 by which the slide 101 of the exoskeleton device 100 is pivotally connected to the slide 201 of the kinematical chain 200.

Figure 6:
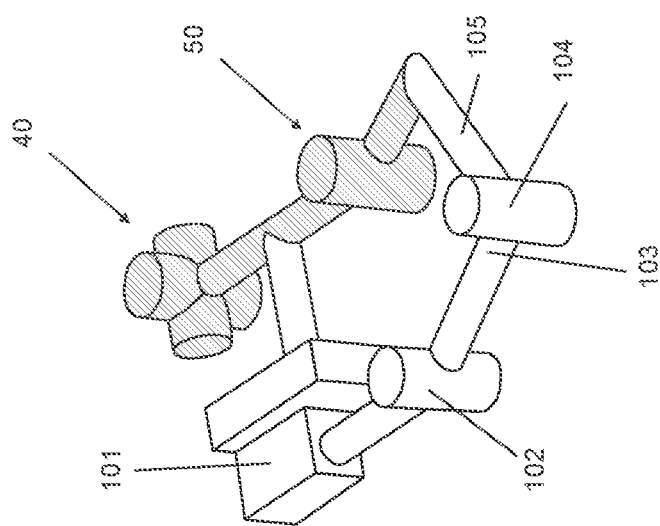
FIG. 6 shows a pattern that is diagrammatically shown in an exemplary embodiment of the exoskeleton device according to the invention mounted to the thumb finger of the hand.

In FIG. 6 a diagram is shown of the exoskeleton device 100 mounted to the thumb finger of the hand. The hatched parts, corresponding to the anatomical parts of the joint, comprise the metacarpal-phalangeal joint 50 and the carpal-metacarpal joint 40.

Figure 7:
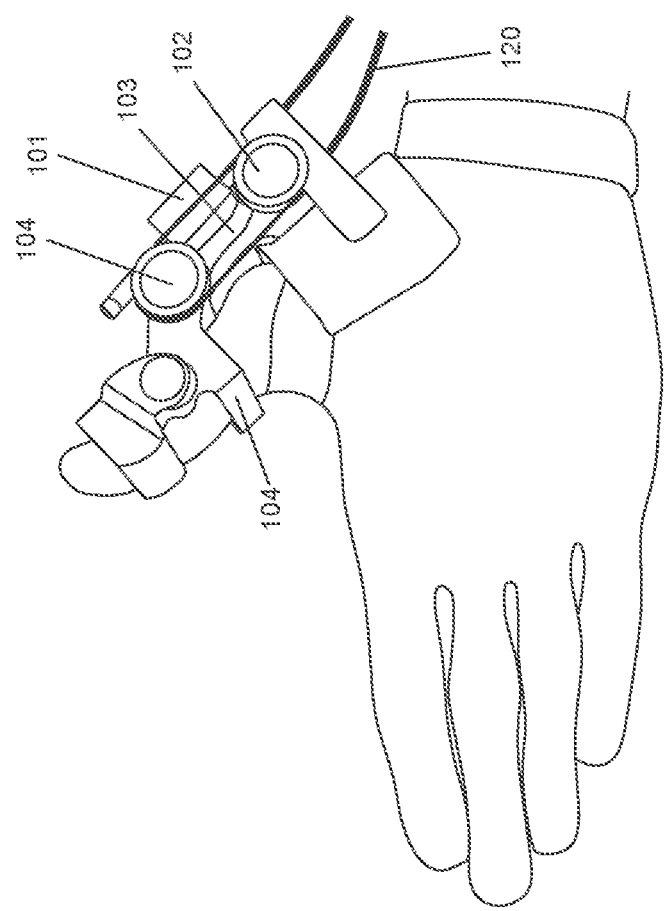
FIG. 7 shows a possible exemplary embodiment of the exoskeleton device of FIG. 6 applied to the thumb finger of the hand.

In FIG. 7 a possible exemplary embodiment is shown of the exoskeleton device 100 applied to the thumb finger of the hand. In this exemplary embodiment, the rotational constraints 102 and 104 are made by means of idle pulleys and the actuating means consists of Bowden cables 120 whose inner wires are wound about such pulleys 102 and 104.

Figure 8:
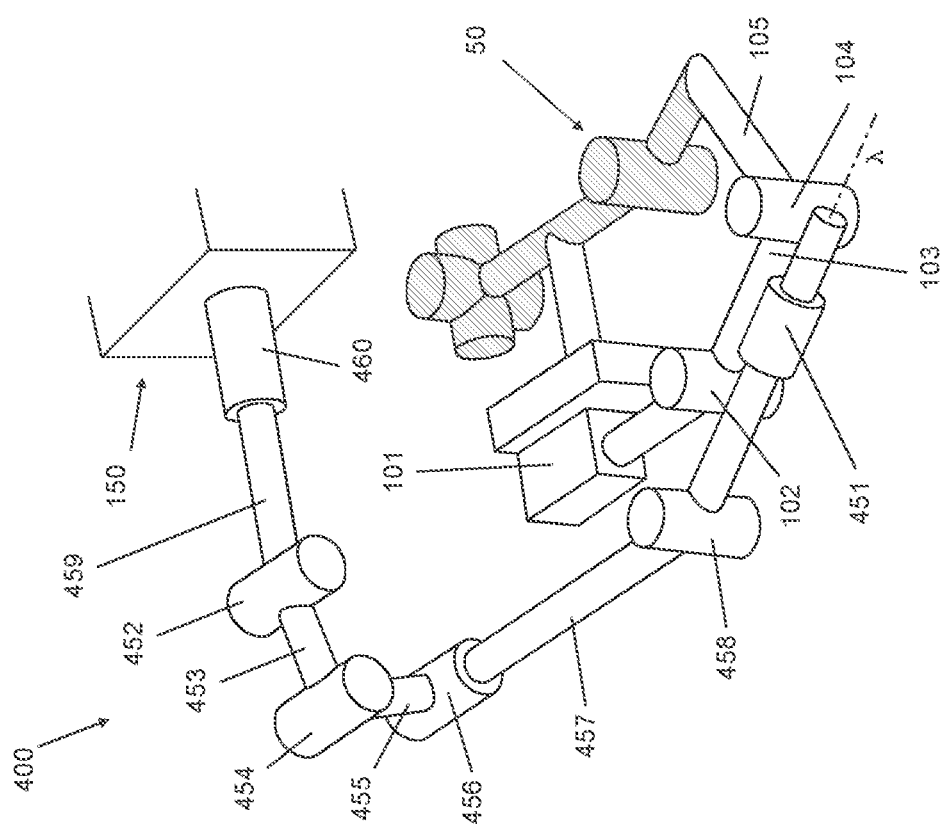
FIG. 8 shows a possible exemplary embodiment of the exoskeleton device shown in FIG. 6.

In FIG. 8 a possible exemplary embodiment is shown of the exoskeleton device 100 shown in FIG. 6, in which between the metacarpal support 150 and the stiff link 103 a kinematical chain 400 is located for the exoskeleton device (100) for assisting the flexion/extension and ab/adduction movements of the carpal-metacarpal joint 40 of the thumb. Such kinematical chain 400 comprises:

- a first shaft 459 arranged to rotate about its own axis with respect to the metacarpal support 150, by a pivotal connection 460;
- a first segment 453 pivotally connected to shaft 459 by a first pivotal constraint 452;
- a second segment 455 pivotally connected to the first segment 453 by a second pivotal constraint 454;
- a second shaft 457 arranged to rotate about its own axis with respect to the second segment 455, by pivotal connection 456;
- a slide 451 pivotally connected to the second shaft 457 by a pivotal constraint 458.

The slide 451 is arranged to slide along a predetermined line λ with respect to the pivotal constraint 458 and is also connected to the stiff link 103.

Rotational constraints 452 and 454 and the rotational coupling 456 and 460 are actuated and are not passive with respect to the movement of the joint 40.

In particular, the operation of the pivotal connection 460 can assist mainly the movement of ab/adduction of the carpal-metacarpal joint 40, whereas the operation of rotational constraints 452 and 454 and of pivotal connection 456 can assist mainly the flexion/extension movement of the carpal-metacarpal joint 40.

Figure 9:
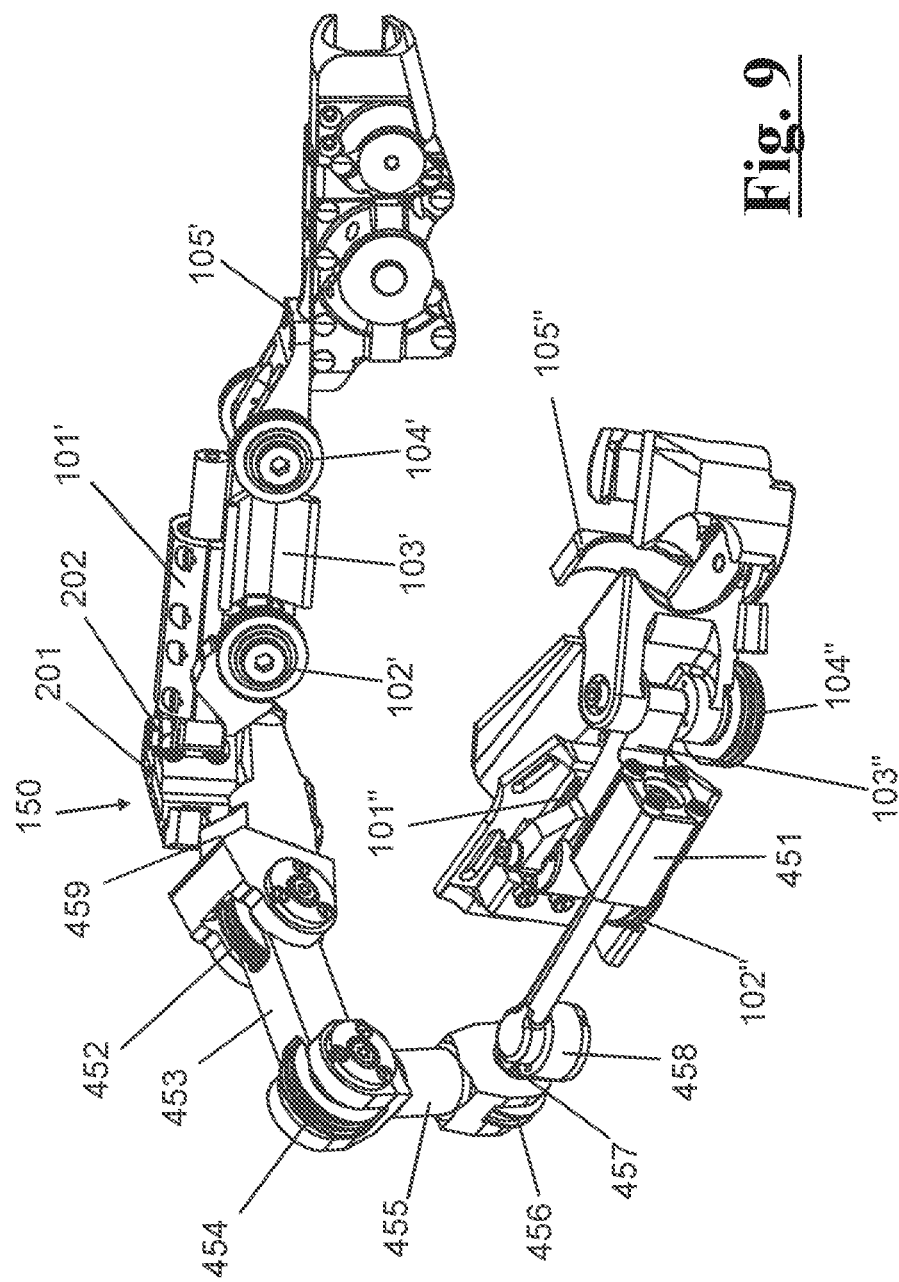
FIG. 9 shows a possible exemplary embodiment of the exoskeleton device mounted both to the index finger and to the thumb finger of the hand.

In FIG. 9 a possible exemplary embodiment is shown of the exoskeleton device applied both to the index finger and to the thumb finger of the hand. For graphical clarity, the numbers of the elements of the device 100 mounted to the index finger are indicated with a prime, whereas the numbers of the elements of the device 100 mounted to the thumb finger are indicated with two primes.

Figure 10:
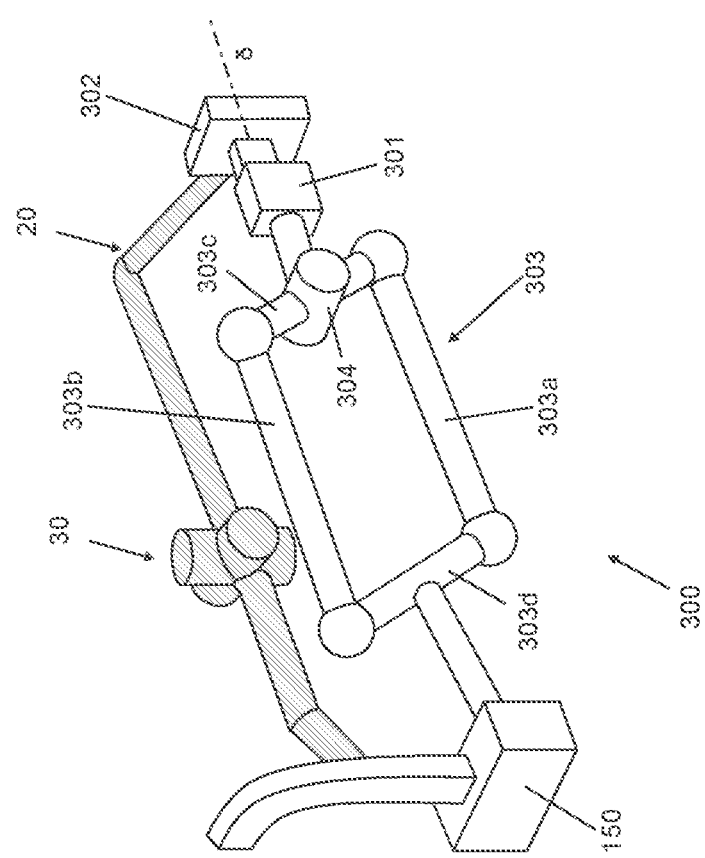
FIG. 10 shows a conceptual diagram of a serial mechanism, operatively connected to the exoskeleton device, arranged to assist the rotation of the anatomical joint of the wrist.

In FIG. 10 a conceptual pattern is shown of a serial mechanism 300, operatively connected to the metacarpal support 150 of the exoskeleton device 100, arranged to assist the flexion/extension of the anatomical joint of the wrist 30, ensuring also free ab/adduction movements. The serial mechanism 300 comprises:

- an ulnar support 302 arranged to be kept integral to a distal portion of the forearm 20;
- a slide 301 arranged to slide with respect to the ulnar support 302 along a predetermined line δ substantially parallel to the longitudinal direction of the forearm;
- an articulated quadrilateral 303 comprising:
    - a first connecting rod 303a and a second connecting rod 303b, parallel to each other and arranged in a direction substantially parallel to the line δ;
    - a first segment 303c pivotally connected to the slide 301 by a pivotal constraint 304;
    - a second segment 303d rigidly connected to the metacarpal support 150.

The first segment 303c and the second segment 303d are adapted to connect between them the ends of the connecting rods 303a and 303b by means of four passive spherical joints, in such a way that the metacarpal support 150 can rotate with respect to the ulnar support 302 about an axis whose position is not determined. In particular, the articulated quadrilateral 303 can adapt passively to the rotation of the anatomical joint of the wrist, according to both the axes that are perpendicular to the longitudinal direction of the forearm, without causing residual constraint forces. The assistance of the flexion/extension movement of the anatomical joint is made by the operation of the pivotal constraint 304.

Figure 11:
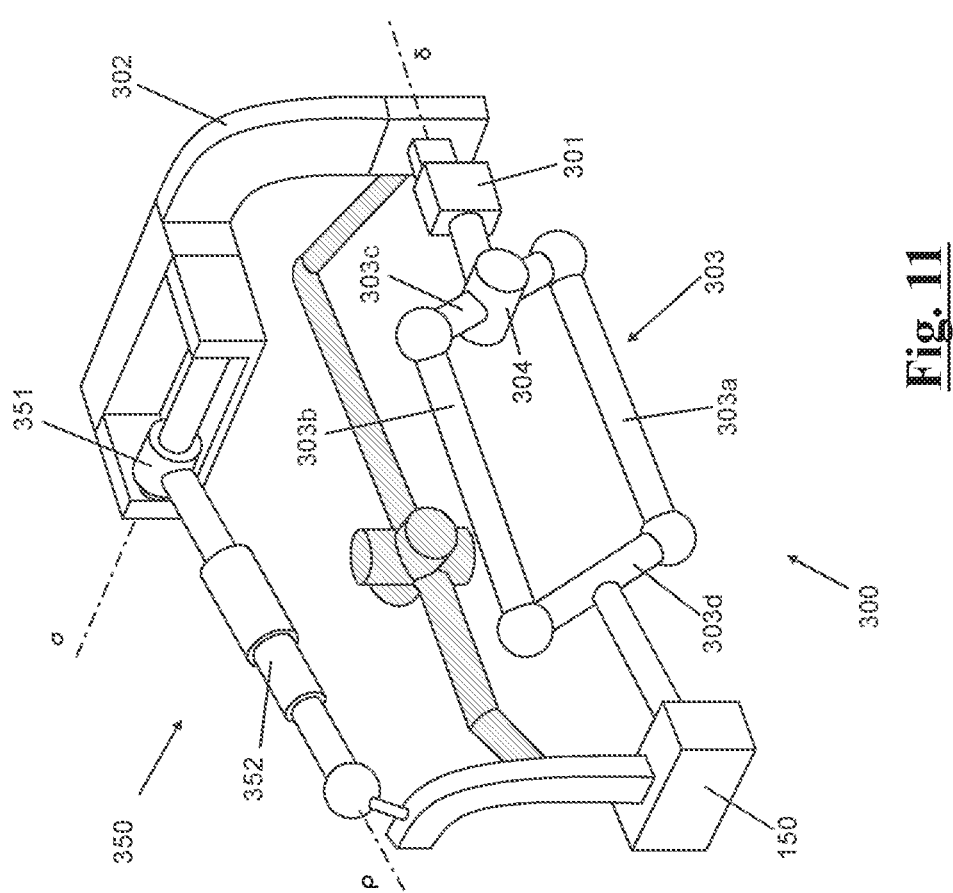
FIG. 11 shows a possible exemplary embodiment of the serial mechanism shown in FIG. 9.

In FIG. 11 a possible exemplary embodiment is shown of the serial mechanism 300 shown in FIG. 9, where a second serial mechanism (350) is further provided, completely passive and operatively connected to the metacarpal support 150, arranged to constrain in a compliant way the matching between the ulnar support 302 and the metacarpal support 150, the second serial mechanism (350) comprising:

- a rotatable slide 351 arranged to slide with respect to the ulnar support 302 along a predetermined line σ and arranged to rotate about the line σ with respect to a same ulnar support 302, said line σ being substantially perpendicular to the line δ;
- a slide 352 arranged to rotate with respect to the rotatable slide 351 along a predetermined line ρ substantially perpendicular to line σ.

The slide 352 is also connected to the metacarpal support 150 by a ball joint.

Figure 12:
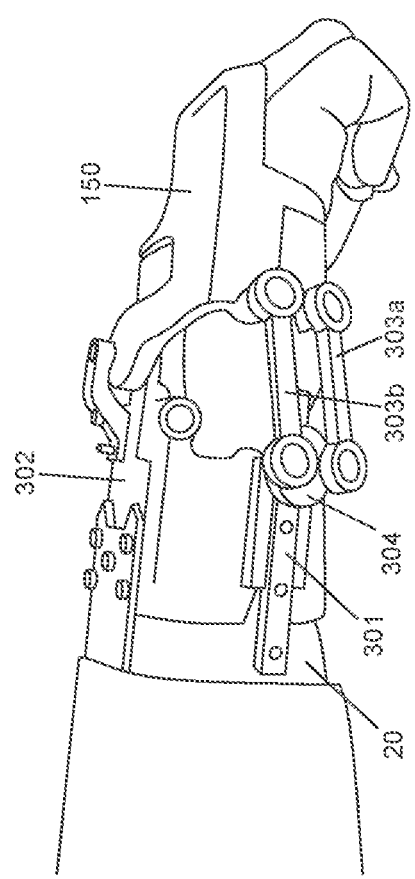
FIG. 12 shows an exemplary embodiment of the serial mechanism of FIG. 10.

In FIG. 12 an exemplary embodiment is shown of the serial mechanism 300 of FIG. 10.

The foregoing description of specific exemplary embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention. It is to be understood that the phraseology or terminology that is employed herein is for the purpose of description and not of limitation.

The work of search that has brought to this invention has received a financing by the Seventh Frame Program of the European Union FP7/2007-2013, in the field of the Project WAY, financing agreement n. 288551.

The invention claimed is:

1. An exoskeleton device for assisting a movement of a metacarpal-phalangeal joint of a hand in a flexion/extension plane Γ of said joint, said metacarpal-phalangeal joint arranged for carrying out a rotation θ about an axis z substantially orthogonal to said flexion/extension plane, the device comprising:

- a metacarpal support arranged to be kept integral to a metacarpal portion of the hand;
- a phalangeal support having a fastening link for fastening to a proximal phalanx;
- a kinematical chain between said metacarpal support and said phalangeal support to provide and carrying out a rotation of said phalangeal support with respect to said metacarpal support;

characterized in that said kinematical chain comprises:

- a metacarpal slide arranged to slide with respect to said metacarpal support along a predetermined line γ, said predetermined line γ arranged in said flexion/extension plane Γ;

a stiff link pivotally connected to said metacarpal slide by a first pivotal constraint;

a second pivotal constraint arranged to connect pivotally said stiff link to said phalangeal support;

an actuating means for causing a first rotation to said stiff link at said first pivotal constraint, and for causing a second rotation to said phalangeal support at said second pivotal constraint, said actuating means being configured for zeroing constraint forces of said exoskeleton device on said metacarpal-phalangeal joint versus said rotation θ, for any position of said metacarpal-phalangeal joint with respect to said exoskeleton device, within a predetermined range.

2. The exoskeleton device according to claim 1, wherein said first rotation and said second rotation of said first and said second pivotal constraints are made by means of respective pulleys arranged at said first and said second pivotal constraints and by at least one cable that causes said pulleys to rotate, in particular said pulleys having a same radius.

3. The exoskeleton device according to claim 2, wherein said actuating means comprises a rotor arranged to cause said first rotation to said first pivotal constraint and at least one cable arranged to connect said first and said second pivotal constraint, such that said first and said second rotation are synchronous to each other.

4. The exoskeleton device according to claim 1, wherein a serial mechanism for a wrist is further provided operatively connected to said metacarpal support and arranged to assist the flexion/extension of the anatomical joint of the wrist, ensuring also free ab/adduction movements, said serial mechanism for the wrist comprising:

an ulnar support arranged to be kept integral to a distal portion of a forearm;

an ulnar slide arranged to slide with respect to said ulnar support along a predetermined line δ, said line δ being substantially parallel to a longitudinal direction of said forearm;

an articulated quadrilateral comprising:
  a first connecting rod and a second connecting rod, parallel to each other and arranged in a direction substantially parallel to said line δ;
  a first segment pivotally connected to said slide by a pivotal constraint;
  a second segment rigidly connected to said metacarpal support;
  said first and said second segments are arranged so that ends of said connecting rods are connected to said first and said second segments by means of four passive spherical joints;
in such a way that said metacarpal support can rotate with respect to said ulnar support about an axis, said articulated quadrilateral being adaptable passively to a rotation of the anatomical joint of the wrist, according to both axes that are perpendicular to a longitudinal direction of the forearm, without causing residual constraint forces.

5. The exoskeleton device according to claim 4, wherein a second serial mechanism is provided, operatively connected to said metacarpal support and is arranged to reinforce a coupling between said ulnar support and said metacarpal support, said second serial mechanism comprising:

a rotatable slide arranged to slide with respect to said ulnar support along a predetermined line σ and arranged to rotate about said line σ with respect to said ulnar support, said line σ being substantially perpendicular to said line δ;

a slide arranged to translate with respect to said rotatable slide along a predetermined line ρ, said line ρ being substantially perpendicular to said line σ, said slide being connected to said metacarpal support by a ball joint.

6. The exoskeleton device according to claim 1, configured for assisting the metacarpal-phalangeal joint of an index finger of said hand, comprising a kinematical chain located between said metacarpal support and said slide, said kinematical chain being configured for assisting a movement of said metacarpal-phalangeal joint in an ab/adduction plane of said metacarpal-phalangeal joint substantially orthogonal to said flexion/extension plane Γ, in such a way that said exoskeleton device can always lay on said flexion/extension plane Γ, said kinematical chain comprises:
  an ab/adduction slide arranged to slide with respect to said metacarpal support along a predetermined line ε, said predetermined line ε arranged in said ab/adduction plane;
  an ab/adduction pivotal constraint by which said metacarpal slide of said exoskeleton device is pivotally connected to said slide of said kinematical chain.

7. The exoskeleton device according to claim 1, configured for assisting the metacarpal-phalangeal joint of a thumb of said hand, comprising a kinematical chain located between said metacarpal support and said stiff link, said kinematical chain being configured for assisting flexion/extension and ab/adduction movements of a carpal-metacarpal joint of said thumb, said kinematical chain comprising:

a first shaft arranged to rotate about its own axis with respect to said metacarpal support, by a pivotal connection;

a first segment pivotally connected to said shaft by a first pivotal constraint;

a second segment pivotally connected to said first segment by a second pivotal constraint;

a second shaft arranged to rotate about its own axis with respect to said second segment, by a pivotal connection;

a slide pivotally connected to said second shaft by a pivotal constraint, said slide arranged to slide with respect to said pivotal constraint along a predetermined line λ and being also connected to said stiff link (103).

8. An exoskeleton device for assisting a movement of a metacarpal-phalangeal joint and of a wrist of a hand, said metacarpal-phalangeal joint arranged for carrying out a rotation θ about an axis substantially orthogonal to a flexion/extension plane Γ of said joint, said device comprising:

a metacarpal support arranged to be kept integral to a metacarpal portion of the hand;

a phalangeal support having a fastening link for fastening to a proximal phalanx;

a kinematical chain between said metacarpal support and said phalangeal support to provide and carrying out a rotation of said phalangeal support with respect to said metacarpal support;

a serial mechanism for the wrist operatively connected to said metacarpal support and arranged to assist the flexion/extension of an anatomical joint of the wrist, ensuring also free ab/adduction movements, said serial mechanism for the wrist comprising an ulnar support arranged to be kept integral to a distal portion of a forearm;

said device characterized in that said serial mechanism for the wrist comprises furthermore:

an ulnar slide arranged to slide with respect to said ulnar support along a predetermined line δ, said line δ being substantially parallel to a longitudinal direction of said forearm;

an articulated quadrilateral comprising:

a first connecting rod and a second connecting rod s, parallel to each other and arranged in a direction substantially parallel to said line δ;

a first segment pivotally connected to said slide by a pivotal constraint;

a second segment rigidly connected to said metacarpal support;

said first and said second segments are arranged so that ends of said connecting rods are connected to said first and said second segments by means of four passive spherical joints;

in such a way that said metacarpal support can rotate with respect to said ulnar support about an axis, said articulated quadrilateral being adaptable passively to the rotation of the anatomical joint of the wrist, according to both the axes that are perpendicular to the longitudinal direction of the forearm, without causing residual constraint forces.

9. The exoskeleton device according to claim 8, wherein a second serial mechanism is provided, operatively connected to said metacarpal support and is arranged to reinforce a coupling between said ulnar support and said metacarpal support, said second serial mechanism comprising:

a rotatable slide arranged to slide with respect to said ulnar support along a predetermined line σ and arranged to rotate about a line σ with respect to said ulnar support, said line σ being substantially perpendicular to said line δ;

a slide arranged to slide with respect to said rotatable slide along a predetermined line ρ, said line ρ being substantially perpendicular to said line σ, said slide being connected to said metacarpal support by a ball joint.

* * * * *